United States Patent
Wolf et al.

(10) Patent No.: US 9,681,904 B2
(45) Date of Patent: Jun. 20, 2017

(54) METHOD AND DEVICE FOR ATTACHING A BONE PLATE

(71) Applicant: DePuy Synthes Products, LLC, Raynham, MA (US)

(72) Inventors: Stefan Wolf, Flumenthal (CH); This Aebi, Grenchen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 570 days.

(21) Appl. No.: 14/146,454

(22) Filed: Jan. 2, 2014

(65) Prior Publication Data

US 2015/0182267 A1    Jul. 2, 2015

(51) Int. Cl.
| | |
|---|---|
| A61B 17/88 | (2006.01) |
| A61B 17/80 | (2006.01) |
| A61B 17/17 | (2006.01) |
| A61B 17/74 | (2006.01) |
| A61B 90/00 | (2016.01) |

(52) U.S. Cl.
CPC ........ *A61B 17/808* (2013.01); *A61B 17/1721* (2013.01); *A61B 17/1728* (2013.01); *A61B 17/1742* (2013.01); *A61B 17/74* (2013.01); *A61B 17/8014* (2013.01); *A61B 2090/062* (2016.02)

(58) Field of Classification Search
None
See application file for complete search history.

(56) References Cited

U.S. PATENT DOCUMENTS

| | | | |
|---|---|---|---|
| 8,025,667 B2 | 9/2011 | Grant et al. | |
| 2008/0281326 A1 | 11/2008 | Watanabe et al. | |
| 2009/0088767 A1 | 4/2009 | Leyden et al. | |
| 2011/0264095 A1* | 10/2011 | Cheng | A61B 17/80 |
| | | | 606/71 |

FOREIGN PATENT DOCUMENTS

EP    0923906    6/1999

* cited by examiner

*Primary Examiner* — Sameh Boles
(74) *Attorney, Agent, or Firm* — Fay Kaplun & Marcin, LLP (57) ABSTRACT

A method and device for attaching a bone plate to a bone includes the steps of placing a first surface of a wire insertion device against the bone, inserting a reference wire through an opening of the wire insertion device extending therethrough from the first surface of the wire insertion device to a second surface of the wire insertion device, removing the wire insertion device from the reference wire and positioning a bone plate on the bone by moving the bone plate in a transverse direction relative to a longitudinal axis of the reference wire so that the reference wire is received within a slot of the bone plate, the bone plate including a first surface facing toward the bone and a second surface opposing the first surface, the slot open to a lateral side surface connecting edges of the first and second surfaces.

10 Claims, 7 Drawing Sheets

METHOD AND DEVICE FOR ATTACHING A BONE PLATE

FIELD OF THE INVENTION

The present invention relates to the field of surgical methods and surgical instruments/devices and, in particular, to a method for attaching a bone plate to a bone; an instrument/device and a bone fixation kit for employment in said method. Specifically, the invention relates to a method and a device for attaching a bone plate to a human proximal femur.

BACKGROUND

In a method for attaching a bone plate to a bone, the patient has been opened and a fracture has been reduced, the bone plate is usually placed against the bone and fixed thereto via suitable bone anchors such as, for example, bone screws, nails, pins or the like. It is, however, essential that correct alignment of the bone plate is achieved prior to fixation of the bone plate. In particular, the position and alignment of the bone anchors is important to ensure a good healing process. Thus, methods for attaching bone plates often utilize a reference wire inserted into the bone through a hole in the bone plate using, for example, a drill sleeve. The reference wire may be, for example, a K-wire (Kirschner wire). The reference wire is inserted into the bone via the hole in the bone plate in a correct orientation and employed for guiding a first bone anchor thereover. Thus the first bone anchor may be cannulated for this purpose. Once the first bone anchor has been placed, further bone anchors are inserted into the bone through corresponding through holes in the bone plate, depending on the application. In particular, in the case of large bone plates, for example, for long bones such as the femur or tibia, the implantation of the bone plate and the correct alignment and positioning can be demanding and troublesome.

The object of the present invention is to provide a method for properly attaching a bone plate to a bone, and a corresponding bone fixation kit, which facilitates proper attachment of the bone plate to the bone.

SUMMARY OF THE INVENTION

According to a first aspect of the invention, a method for attaching a bone plate to a bone comprises placing a first surface of a wire insertion device against the bone. The wire insertion device preferably comprises a base with a first side formed to be placed against the bone in a defined manner, and a second side opposing the first side.

In one exemplary embodiment, an opening extends through the base of the wire insertion device from the first side to the second side. The opening may be sized and shaped to receive a reference wire and guide it in a defined direction. Preferably, the wire insertion device comprises a handle or leg extending away from the first side. This facilitates the handling of the wire insertion device.

The reference wire is guided into the opening of the wire insertion device and into the bone. A surface of the wire insertion device corresponds to a surface of the bone against which it is to be positioned such that the bone plate may be placed against the bone in a defined manner. An opening of the wire insertion device possesses a length selected to be sufficient for exact guidance and an alignment corresponding to the desired direction of the reference wire. Thus, accurate insertion of the reference wire into the bone is enabled.

In a next step, the wire insertion device may be removed from the reference wire inserted into the bone. The wire insertion device may be withdrawn from the bone along the longitudinal extension of the reference wire.

In an exemplary embodiment, the wire insertion device is first removed and then the bone plate is positioned on the bone. The bone plate may include a slot open toward a lateral side surface connecting a first, bone-facing surface of the bone plate to a second surface of the bone plate opposing said first surface. The bone plate may be positioned along the bone by moving the bone plate in a transverse direction with respect to a longitudinal axis of the reference wire until the wire is received within the slot of the bone plate.

The exemplary method facilitates positioning of the bone plate on the bone since a reference wire is inserted into the bone prior to the actual positioning of the bone plate. The bone plate itself is only advanced to the bone in a subsequent step. The slot in the bone plate allows it to be advanced to the reference wire which has already been inserted into the bone. In a preferred embodiment, the bone plate is moved laterally, i.e., in a direction transverse to the longitudinal axis of the reference wire. The bone plate may be inserted into the patient and positioned relative to the reference wire through a skin incision, and the slot, unlike a hole closed around its circumference, allows the bone plate to be advanced to the reference wire after the bone plate has been inserted into the body. In other words, as the slot is open, the bone plate does not need to be slid over the wire through the incision until it reaches the bone plate but can be advanced into the body and then the plate can be maneuvered, for example, until the slot is adjacent to the site at which the wire enters the bone. The plate can then be slid so that the wire enters the slot. Inserting the reference wire into the bone with a separate wire insertion device also simplifies the method, since the wire insertion device has smaller dimensions than the bone plate and can be more easily inserted into the patient and placed against the bone.

In an exemplary embodiment, the surface of the wire insertion device that is configured to be placed against the bone has a surface shape corresponding to the shape of the bone surface. According to one exemplary embodiment, the wire insertion device is configured to be placed against the human proximal femur and, in particular, the greater trochanter of the proximal femur. To prevent it from slipping off the bone surface, or at least to reduce such slip, the surface of the wire insertion device that is configured to be placed against the bone may include at least one mandrel protruding therefrom. It will be appreciated that other surface structures that reduce or prevent slippage can also be provided, such as for example ribs, teeth, cusps or other projections.

To further facilitate its handling, the wire insertion device may include a handle. In an exemplary embodiment, the wire insertion device may include a leg extending therefrom and including a handle coupling at an end thereof to which a removable hand grip is fastenable.

According to one exemplary embodiment, the method comprises the step of mounting a positioning device or aiming or guide block on the bone plate before positioning the bone plate on the bone. The bone plate is then positioned on the bone by means of the positioning device mounted on the bone plate. The positioning device may comprise a base having a first surface configured to be placed against the bone plate in a defined manner, and a second surface opposing the first surface. A shape of a surface of the positioning device facing the bone plate may correspond to a shape of the second surface of the bone plate to facilitate the aligning and mounting of the positioning device on the bone plate. In one exemplary embodiment, the positioning device is positioned against the bone plate and aligned relative thereto prior to being fixed to the bone plate.

According to one exemplary embodiment, the positioning device includes a slot extending therethrough between the first and second surfaces of the base of the positioning device and open to a lateral surface of the base. Upon mounting of the positioning device on the bone plate, the slot of the positioning device may be aligned with the slot of the bone plate. This allows the reference wire to engage both the slot of the bone plate and the slot of the positioning device upon positioning of the bone plate on the bone. Because the positioning device thus also engages the reference wire, the aligning and positioning of the bone plate on the bone is further improved.

According to one exemplary embodiment, a protection sleeve comprises a first axial passageway and a second axial passageway parallel thereto. The sleeve is thus designated as a double sleeve. The sleeve having the first and second axial passageways may be inserted into the slot of the positioning device and into a through hole open to the lateral side surface via the slot. Thus, the sleeve may be guided along the reference wire via its first axial passageway. The sleeve may be guided via the reference wire after the bone plate has been advanced to the reference wire. It will be understood by those of skill in the art, however, that it is also possible to partially guide the sleeve along the reference wire before the bone plate is moved to a desired position along the bone relative to the reference wire, and pushed further in the direction of the bone once the bone plate has been moved to the desired position so that the sleeve is received in the slot and the through hole of the positioning device.

The sleeve also serves as a drill sleeve. A tool for producing a hole in the bone such as, for example, a drill bit of a drill, a ram, a K-wire or the like, may be inserted into the second axial passageway of the sleeve. Through the provision of a sleeve having two axial passageways the method is simplified, because one of the axial passageways is configured to receive the reference wire while the other axial passageway is configured to receive at least one tool. Thus, no special items such as cannulated bone anchors are necessary.

Once a hole has been drilled into the bone via the second axial passageway, a bone anchor may be inserted into the bone, through the through hole of the positioning device and through a through hole of the bone plate. Preferably, this is the first bone anchor by means of which the bone plate is fixed on the bone. The first bone anchor is of crucial importance because it constitutes a reference for further bone anchors.

According to a further exemplary embodiment, there is provided a flexible ruler or measuring device which may be coupled to the sleeve or to other drill sleeves. Upon insertion of a hole producing tool, such as a drill, which may have a diameter significantly greater than that of the drill bit and/or drill sleeve, the flexible measuring device can bend away from a longitudinal axis of the drill sleeve, in particular of the second axial passageway of the double sleeve. This facilitates measuring of the depth of a hole in the bone, as the hole producing tool need not be removed to measure the depth of the hole. The flexible measuring device can remain mounted on the sleeve as it is able to bend away from the longitudinal axis of the sleeve.

For the insertion of further bone anchors, an aiming device is used which is configured for guiding at least one drill sleeve for targeted drilling of a hole into the bone. In particular, the aiming device has a first surface and a second surface opposing the first surface, a through hole extending through the aiming device between the first and second surfaces sized and shaped to receive at least one drill sleeve. In an exemplary embodiment, the aiming device is mountable on the positioning device. In particular, the aiming device may be coupled to a handle coupling of the positioning device, on which a hand grip is also mountable. The aiming device may be positioned relative to the bone plate by means of the positioning device.

According to a further exemplary embodiment, an orientation wire is inserted into the bone before the wire insertion device is placed against the bone. Once the orientation wire has been inserted into the bone, the wire insertion device may be placed against the bone such that the reference wire inserted by means of the wire insertion device lies in a plane parallel to a plane in which the previously inserted orientation wire lies. The orientation wire may be inserted into the bone under the control of an imaging method. The orientation wire is used to aid in determining the correct direction of the reference wire with respect to the wire insertion device. For example, the orientation wire may be inserted into the femur parallel to the femoral neck. The reference wire is then inserted in a plane parallel, in a lateral view, to a plane in which the orientation wire lies. In this way correct alignment of the reference wire is ensured. Once the reference wire is in place, the orientation wire may be removed. The reference wire is preferably inserted through a center of the femoral neck.

According to a further aspect of the invention, a bone fixation kit which comprises the wire insertion device, the bone plate and the positioning device as described. The bone fixation kit also comprises at least one reference wire and at least one sleeve, preferably a double sleeve, as described above. Further, the bone fixation kit may comprise the flexible measuring device and the aiming device as described.

BRIEF DESCRIPTION OF THE DRAWINGS

The preceding summary of the invention as well as the following description of an exemplary embodiment will become more easily understandable in the light of the attached drawings. An exemplary embodiment of the invention will be described hereinafter with reference to the accompanying drawings. It will be appreciated, however, that the application is not limited to the exemplary embodiment shown. The drawings show.

DETAILED DESCRIPTION

The present invention may be further understood with reference to the following description and the appended drawings, wherein like elements are referred to with the same reference numerals. The present invention is directed to a system and method for treating a bone. In particular, exemplary embodiments of the present invention describe a system and method for fixing a bone plate to a bone. It will be understood by those of skill in the art that although the exemplary embodiment is specifically described with respect to the proximal femur, the system and method of the present embodiment may be utilized for any of a variety of bones and, in particular, for long bones.

FIGS. 1-9 show steps of a method for attaching a bone plate to a bone. In an exemplary embodiment, a bone plate 8 is to be attached to a human proximal femur 1, in particular in the region of the greater trochanter 2. According to the method exemplary embodiment, the patient may first be positioned on an operating table. Using a template, the length of a bone plate to be fixed to the femur 2 may be determined in an X-ray image of the leg. For example, a template may be positioned on the skin to overlap with the subjacent bone in the X-ray image to determine the length of the bone plate to be implanted.

Figure 1:
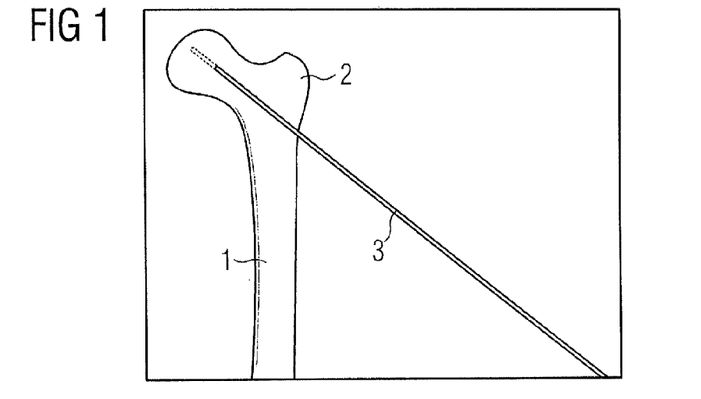
FIGS. 1-9 show steps of an exemplary method for attaching a bone plate to a bone.

After the patient has been opened, i.e. a corresponding incision made, to expose the fracture, the fracture is reduced using known methods. For example, the fracture may be reduced via Schanz screws, forceps for compressing the fracture, in particular the bone segments separated by a bone gap, or other suitable instruments. To ascertain the correct alignment of the bone, in particular the anteversion, an orientation wire 3 is first inserted into the bone. The orientation wire may be inserted into the bone under the control of an imaging method. The orientation wire 3 may be inserted into the bone using, for example, an imaging method. FIG. 1 shows the orientation wire 3 inserted into the bone. The orientation wire 3 can be inserted into the femur through the incision or percutaneously. The orientation wire 3 may be inserted into a femoral head of the bone along an axis parallel to an axis of the femoral neck. The orientation wire 3 serves as an orientation aid for the reference wire 5 to be inserted into the bone.

Figure 2:
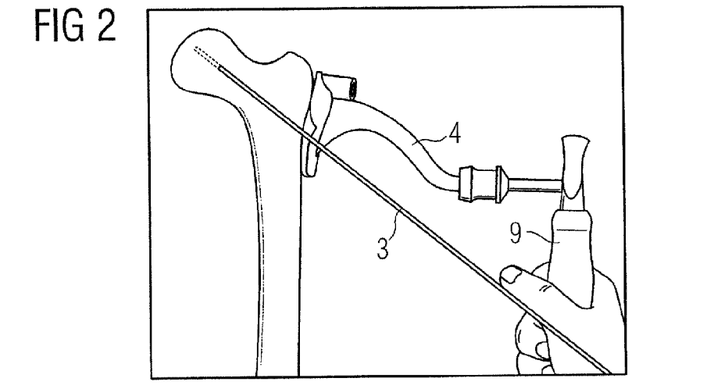

As represented in FIG. 2, in a next step of the method, a wire insertion device 4 is placed against the femur 1, in particular, against the greater trochanter 2. The wire insertion device 4 may include a surface shaped to correspond with the surface of the femur 1, in particular the greater trochanter 2. Due to the relatively small dimensions, in particular in comparison to a bone plate, the wire insertion device 4 may be easily placed against the bone 1 through the incision. The surgeon can guide and hold the wire insertion device 4 by means of a hand grip 9 fastened to a leg 13 of the wire insertion device 4.

Figure 3:
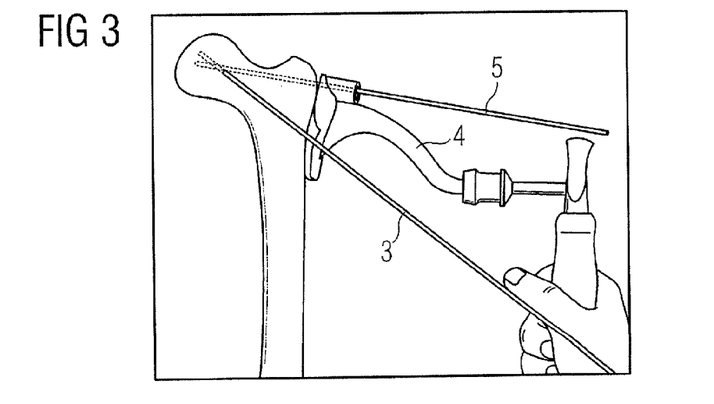
Figure 4:
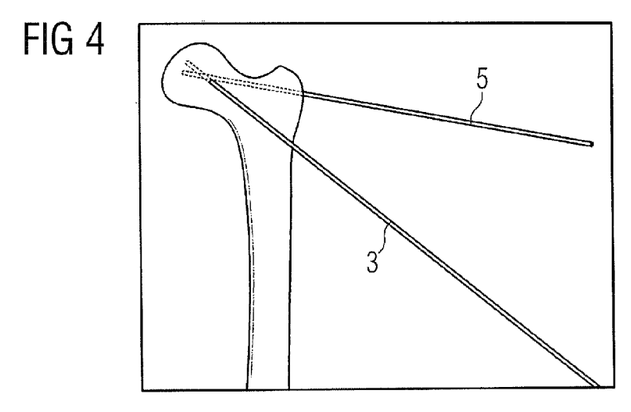
Figure 5:
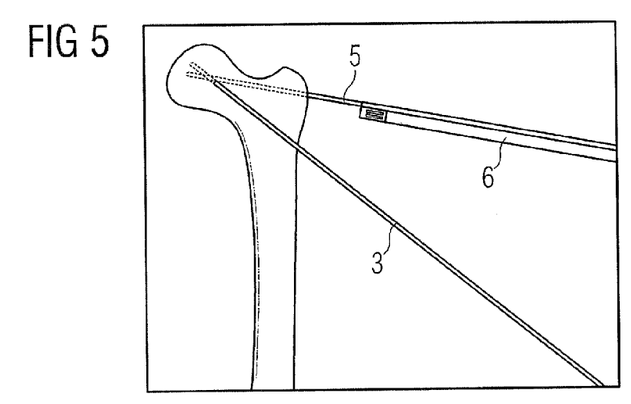
Figure 19:
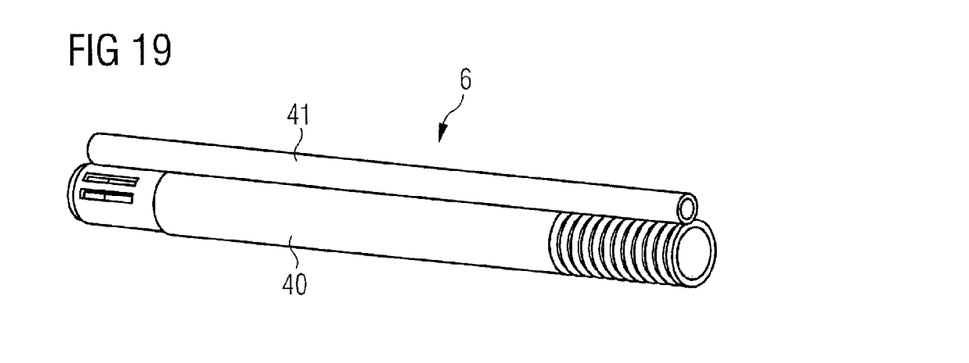
FIG. 19 shows a perspective view of a double sleeve according to an exemplary embodiment of the present invention.

In a next step, as represented in FIG. 3, a reference wire 5 is inserted into the femur 1 through an opening in the wire insertion device 4. In an exemplary embodiment of the method, the reference wire 5 may be inserted through a center of the femoral head. In FIG. 4, the orientation wire 3 and the reference wire 5 are represented in their position inserted into the femur 1. The orientation wire 3 and the reference wire 5 are located in two planes parallel to each other, in a lateral view of the femur 1. A protection sleeve 6 having a first axial passageway 41 and a second axial passageway 40, as seen in FIG. 19, is guided along the reference wire 5 via the first axial passageway 41, as represented in FIG. 5.

Figure 6:
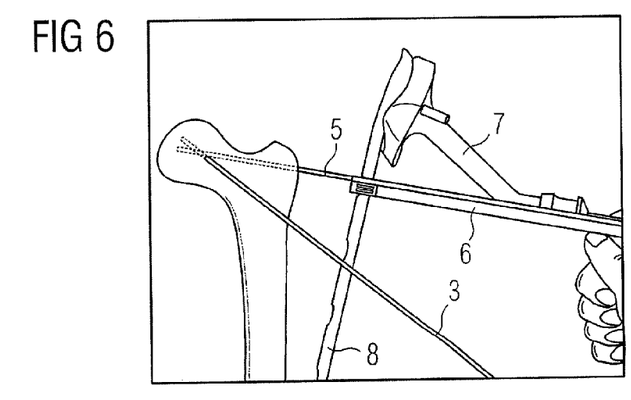
Figure 7:
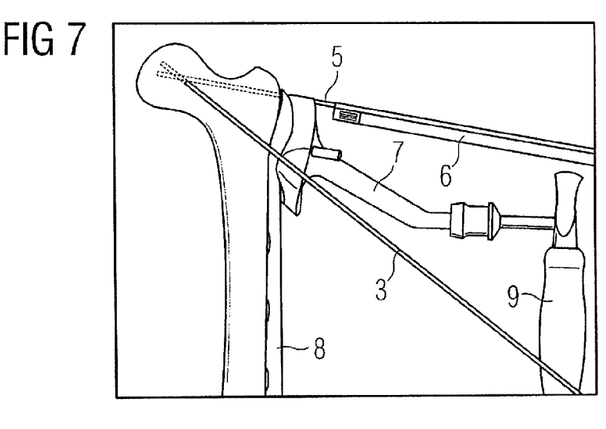
Figure 8:
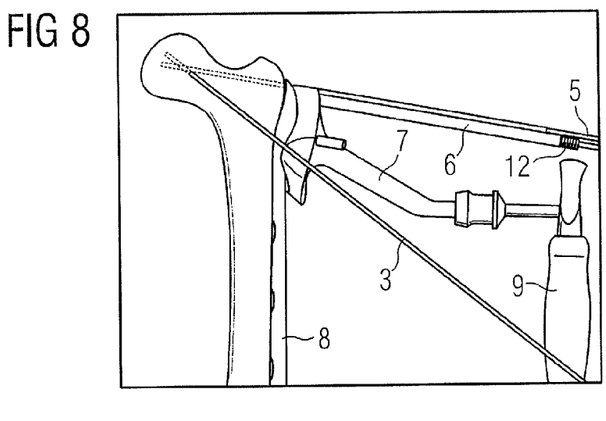

As represented in FIGS. 6-8, the reference wire 5 is employed for the alignment and positioning of the bone plate 8. As seen, in particular, in FIG. 6, the bone plate 8 is inserted into the patient via a positioning or aiming device 7. For this purpose, the positioning device 7 is preferably already connected to the bone plate 8 before an incision is made. FIG. 6 shows a snapshot during the motion of the insertion of the bone plate 8 via of the positioning device 7. The bone plate 8 and the positioning device 7 are inserted through the incision with respect to the reference wire 5. The bone plate 8 and the positioning device 7 may be moved transversely relative to a longitudinal direction of the reference wire 5, as represented in FIG. 7. In particular, the advancing of the bone plate 8 to the reference wire 5 is effected in a proximal to a distal direction along the femur 1. The bone plate 8 and the positioning device 7 respectively have slots at their proximal ends for this purpose, as to be described in detail hereinafter. In other words, the bone plate 8 and the positioning device 7 are inserted through the incision and moved distally along the bone 1 until the slots at the proximal ends of the bone plate 8 and the positioning device 7 receive the reference wire 5.

Once the bone plate 8 has been positioned over a desired portion of the bone—e.g., with the reference wire 5 received within the slot at the proximal end of the bone plate 8—the sleeve 6 is pushed forward until it engages the positioning device 7. As represented in FIG. 8, corresponding tools 12 for drilling a hole may be inserted through the second axial passageway 40 of the sleeve 6 to drill a hole in the bone for receiving a bone anchor. This serves in particular for inserting a first bone anchor for fixing the bone plate 8 to the bone 1 through the slot at the proximal end of the bone plate 8. The tool 12 may be, for example, a drill bit, a ram, a Kirschner wire (K-wire), a trocar, or the like. Once the first bone anchor has been placed, the sleeve 6, the reference wire 5 and also the orientation wire 3, if any, can be removed. It will be understood by those of skill in the art that the orientation wire 3 may have already been removed, after placement of the reference wire 5.

Figure 9:
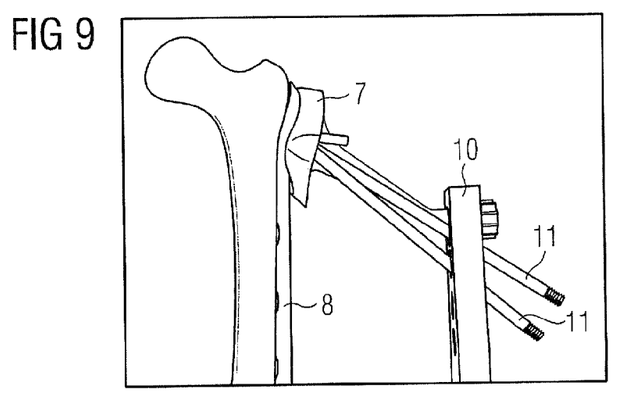

As represented in FIG. 9, the positioning device 7 is then coupled to an aiming device 10 which is employed for targeted drilling of further holes into the bone 1. One or a plurality of protective sleeves 11 may be guided through the aiming device 10 at different angles. Drill sleeves may be inserted through the protective sleeves 11 to guide drill bits therethrough to drill holes through the proximal head portion of a bone plate 8 for placing bone anchors in the femoral neck. Similarly, protective sleeves may also be guided through the aiming device 10 to drill holes into the subjacent bone 1 in the distal shaft portion of the bone plate 8 so that corresponding bone anchors may be inserted into subjacent bone 1 via the distal shaft portion of the bone plate 8.

Figure 10:
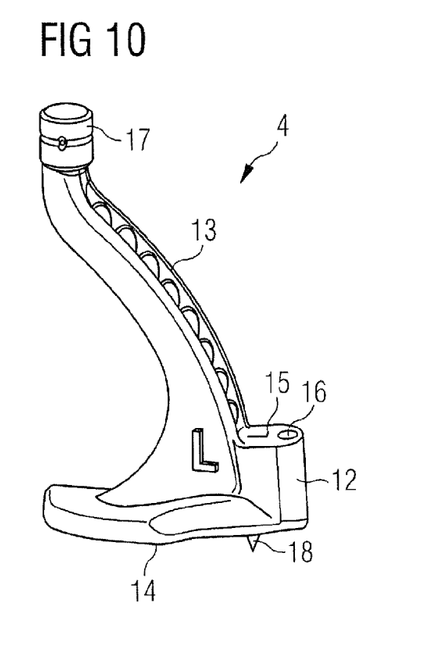
FIG. 10 shows a perspective view of a wire insertion device according to an exemplary embodiment of the present invention.
Figure 11:
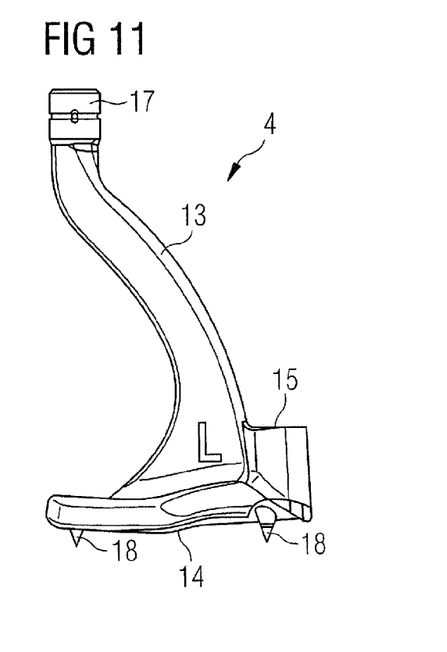
FIG. 11 shows a side view of the wire insertion device of FIG. 10.
Figure 12:
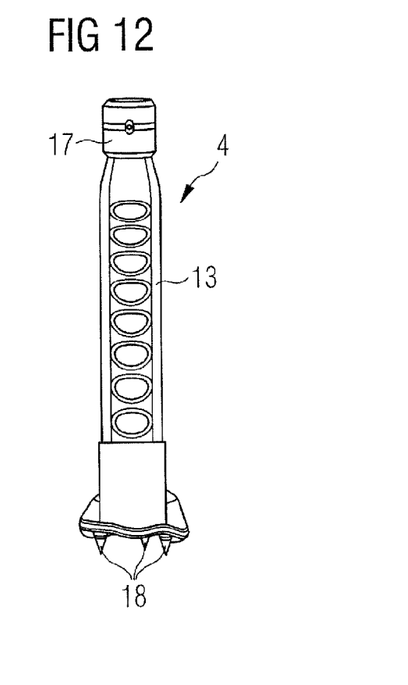
FIG. 12 shows another side view of the wire insertion device of FIG. 10.
Figure 13:
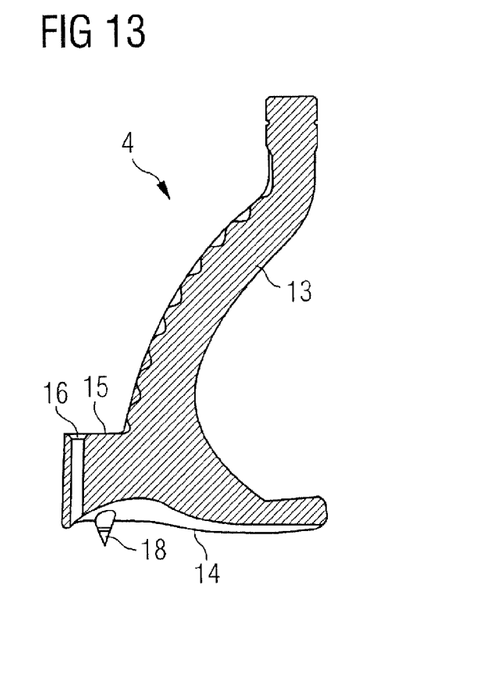
FIG. 13 shows a cross-sectional view of the wire insertion device of FIG. 10.

FIGS. 10-12 show represented different views of the wire insertion device 4, and FIG. 13 shows a sectional representation thereof. The wire insertion device 4 includes a base 12 which has a surface 14 configured to be placed against the greater trochanter 2 of the bone 1, and a surface or side 15 opposing said surface 14. From the non-bone-facing side 15 there extends a leg 13 which has a handle coupling 17 at its free end. A removable hand grip 9 may be fastened to the handle coupling 17, as seen, for example, in FIGS. 2 and 3. The hand grip 9 is removable from the wire insertion device 4 to be sterilized separately therefrom. The surface 14 may be formed, e.g., shaped, to be placed against the bone 1 and, in one exemplary embodiment, may include three mandrels 18 for engaging the surface of the bone to impede or prevent slipping of the wire insertion device 4 relative to the bone. The mandrels 18 may be, for example, protrusions extending from the surface 14 and including a sharp tip for engaging the surface of the bone. Although the exemplary embodiment specifically shows and describes three mandrels 18, it will be appreciated that a smaller or greater number of mandrels, or other suitable structures may be provided without departing from the scope of the invention.

As seen in particular in the sectional representation in FIG. 13, an opening 16 extends through the base 12 from the surface 14 to the opposing side 15. The opening 16 is sized and shaped to guide the reference wire 5. To facilitate the insertion of the reference wire 5, the opening 16 may be chamfered at an end facing the side 15. A length of the opening 16 is selected to be sufficient to guide the reference wire 5. The diameter of the opening 16 is also chosen accordingly. For example, the inner diameter of the opening 16 may correspond to an outer diameter of the reference wire 5. The diameter of the opening 16 may range, for example, between to 2-15 mm. The axial length of the opening 16 may range, for example, between 5-50 mm.

According to an alternative embodiment (not represented), the opening 16 may be configured as a lateral slot so that it is open to a lateral side surface of the base 12 so that the wire insertion device 4 may be moved away from the reference wire 5 in a direction transverse to the longitudinal axis of the reference wire 5. In this embodiment, the opening 16 may be similar to the design of the positioning device 7 described in further detail below. In this embodiment, the sleeve 6 is preferably employed for inserting the reference wire 5.

Figure 14:
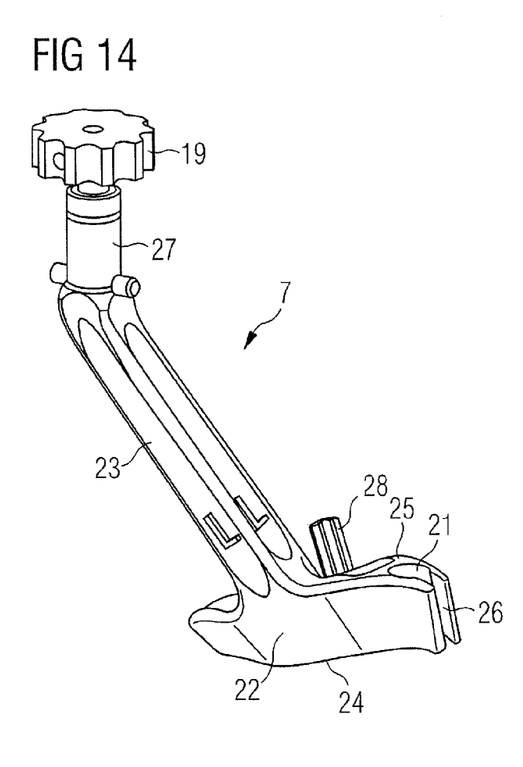
FIG. 14 shows a perspective view of a positioning device according to an exemplary embodiment of the present invention.
Figure 15:
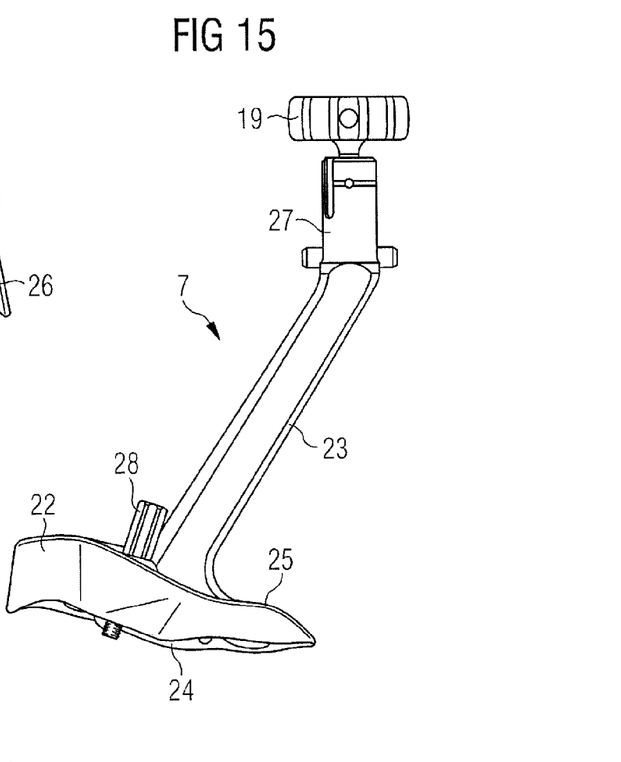
FIG. 15 shows a side view of the positioning device of FIG. 14.
Figure 16:
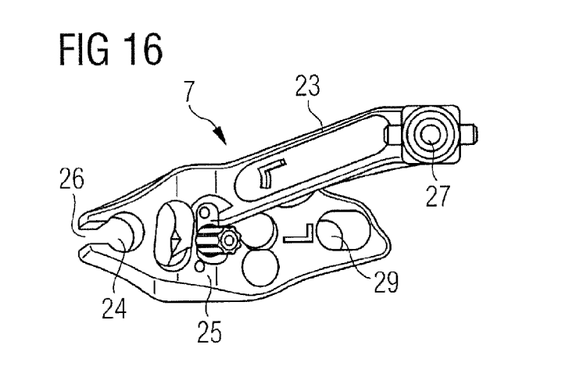
FIG. 16 shows a top plan view of the positioning device of FIG. 14.

In FIGS. 14-16, different views of a positioning device 7 are represented. The positioning device 7 includes a base 22 with a lower surface 24 configured to be placed against a bone plate 8. For example, the lower surface 24 may be formed to include a curve corresponding to a curve of the bone plate 8. Opposing the surface 24 is an upper surface 25 from which a leg 23 extends. The leg 23 has at its free end a coupling 27 that may be used for fastening the hand grip 9, described above with respect to the wire insertion device 4, as shown, in particular, in FIGS. 7 and 8. The coupling 27 may also be used for fastening the aiming device 10, as represented in particular in FIG. 9. The aiming device 10 may be coupled to the coupling 27 via, for example, a knurled-head screw 19. It will be understood by those of skill in the art that other suitable fastening mechanisms can be provided as an alternative to the knurled-head screw 19. In one exemplary embodiment, the coupling 27 is formed such that the aiming device 10 can be attached to the aiming device 10 in only one orientation to guarantee a desired alignment of the aiming device 10 relative to the bone plate 8. The positioning device 7 may be fastened to the bone plate 8 via, for example, a screw 28, preferably before the patient is opened. It will be understood by those of skill in the art that instead of the screw 28, the positioning device 7 may also be coupled to the bone plate 8 via a snap connection, a bayonet lock or any other suitable fixing arrangement. In another embodiment, the positioning device 7 may rest against the bone plate 8 in a proper alignment via corresponding features of the positioning device 7 and the bone plate 8. In particular, the lower surface 24 may include a plurality of protrusions (e.g., ball shaped protrusions) extending therefrom and sized and shaped to be received within corresponding openings extending through a surface of the bone plate 8. The balls will ensure that the positioning device 7 is properly aligned with the bone plate 8.

The positioning device 7 includes a through hole 21 extending through the base 22 between the surfaces 24, 25 and open to a lateral side surface extending between the surface 24 and the surface 25 via a slot 26. In the represented embodiment, the slot 26 and the through 21 are interconnected. The slot 26 and the through hole 21 are sized and shaped to receive the sleeve 6. In particular, the first axial passageway 41 of the sleeve 6 is received in the slot 26 while the second axial passageway 40 of the sleeve 6 is received in the through hole 21.

The first axial passageway 41 of the sleeve 6 has a smaller diameter than the second axial passageway 40 of the sleeve 6. The first axial passageway 41 serves only to receive the reference wire 5, whereas the second axial passageway 40 is sized and shaped to receive a tool such as, for example, a drill bit 42 which is described in further detail below. The drill bit 42 may be guided through the second axial passage 40 to the bone to produce a hole in the bone. Thus, the second axial passageway 40 may have a diameter greater than that of the first axial passageway 41.

Figure 17:
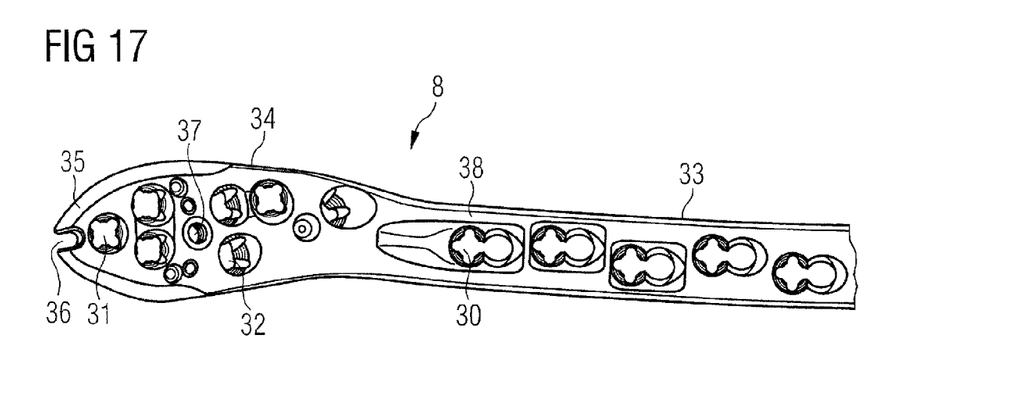
FIG. 17 shows a top plan view of a portion of a bone plate according to an exemplary embodiment of the present invention.
Figure 18:
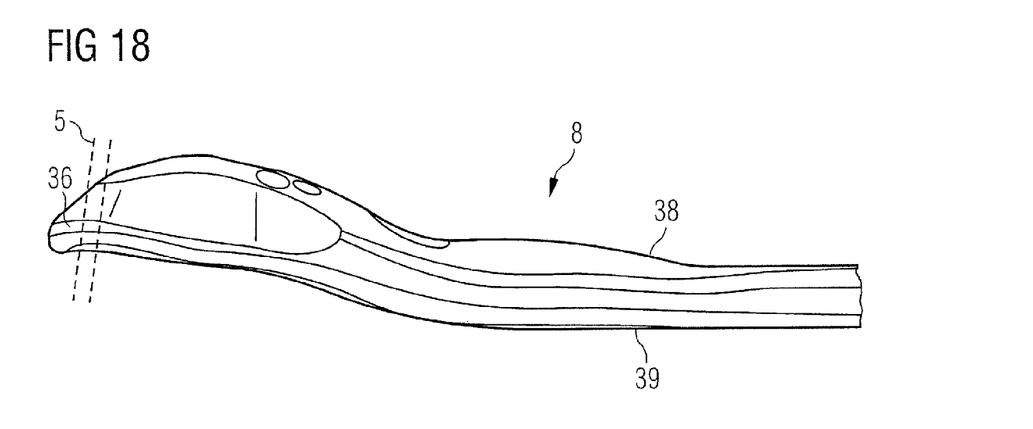
FIG. 18 shows a side view of the bone plate of FIG. 17 with an indicated reference wire.

FIGS. 17 and 18 show a part of the bone plate 8 configured to be placed against the greater trochanter 2. The bone plate 8 comprises a head portion 34 and a shaft portion 33. The head portion 34 may have a curvature corresponding to a curvature of the greater trochanter 2. The bone plate 8 may include through holes 30, 31, 32 which extend through the bone plate 8 from a bone-facing surface 39 to a non-bone-facing surface 38 thereof. The through holes 30 extend through the shaft portion 33 of the bone plate 8 and are formed as combination holes which have a portion for variable-angle fixation of a head locking screw, as well as a compression hole portion for receiving a bone anchor having a smooth screw head. The through holes 31, 32 extend through the head portion 34 of the bone plate 8 and are preferably formed as variable-angle locking holes.

The bone plate 8 further includes a slot 36 which extends through the head portion 34 from the bone-facing surface 39 to the non-bone-facing surface 38 and which opens to a lateral side surface 35 connecting edges of the bone-facing and non-bone-facing surfaces 39, 38. The slot 36 is located, in this embodiment, at the proximal end of the head portion 34 of the bone plate 8. As represented in FIG. 18, the slot 36 is configured to engage the reference wire 5. The slot 36 may be angled relative to a plane of the shaft portion 33 of the bone plate 8, as also seen in FIGS. 7 and 8.

As made clear by FIGS. 16 and 17, the positioning device 7 and the bone plate 8 are adapted to each other such that the slot 26 of the positioning device 7 is aligned with the slot 36 of the bone plate 8 when the positioning device 7 is mounted on the bone plate 8. Accordingly, the through hole 21 of the positioning device 7 is aligned with a proximal most through hole 31 of the bone plate 8. The bone plate 8 may further include a threaded hole 37 extending through the head portion 34 from the surface 39 to the surface 38 for receiving the screw 28 of the positioning device 7 so that the positioning device 7 may be coupled to the bone plate 8.

The employment of the wire insertion device 4, as well as of the positioning device 7 with the slot 26 and the bone plate 8 with the slot 36, facilitates the attachment of the bone plate 8 to the bone 1 since the reference wire 5 can be inserted into the bone 1 by means of the wire insertion device 4 before the positioning of the bone plate 8, and the bone plate 8 can then be moved into position along the bone 1 with respect to the reference wire 5 via the slot 36, as indicated in FIG. 18.

Figure 20:
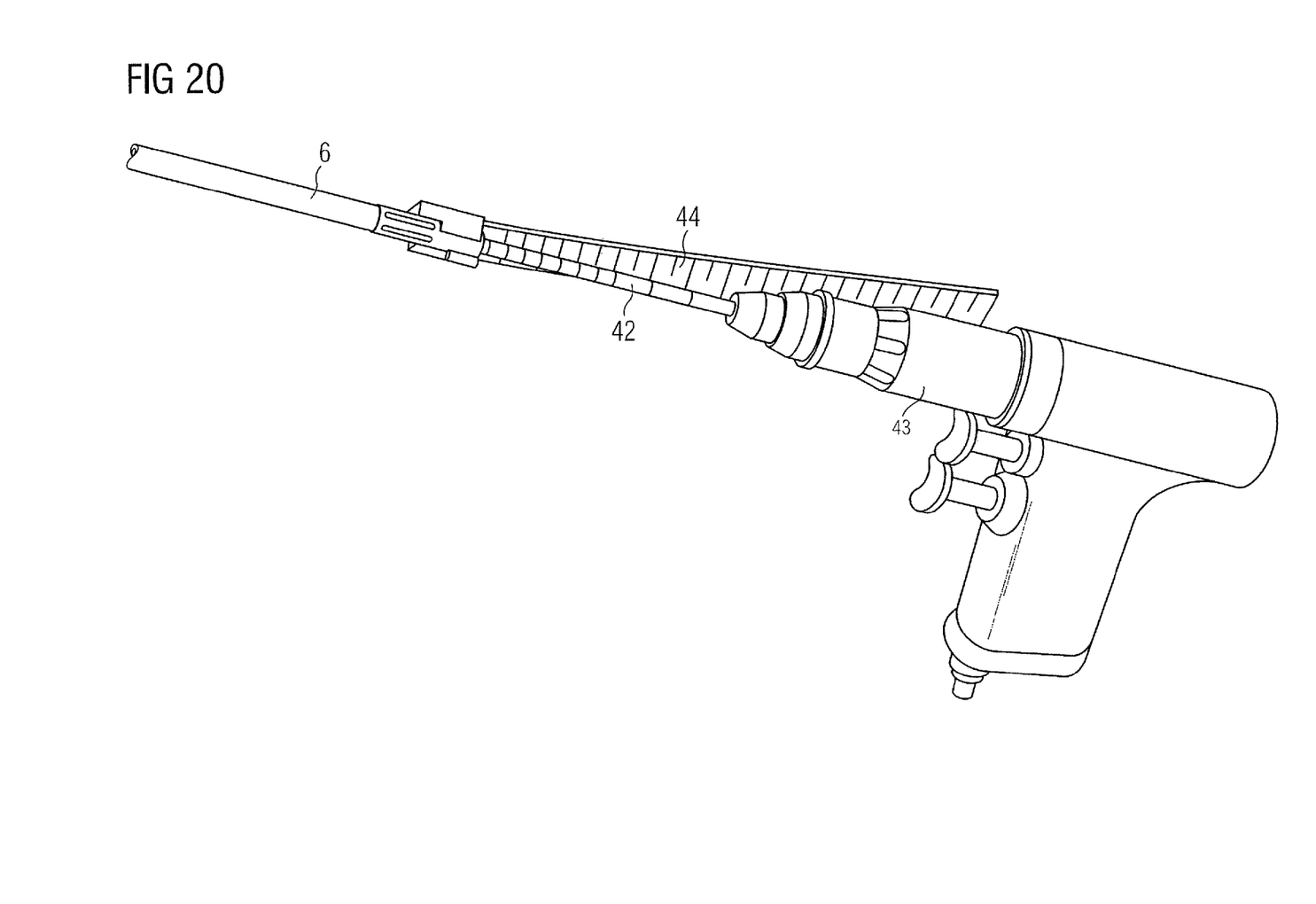
FIG. 20 shows a measuring instrument according to an exemplary embodiment of the present invention.

To determine the depth of bone anchor holes to be formed in the bone 1, a measuring instrument 44 may be provided, as represented in FIG. 20. The measuring instrument 44 can be fastened, for example, to a drill sleeve which may be inserted through the sleeve 6, but also through the protective sleeve 11. The measuring instrument 44 may be formed as a flexible ruler or measuring device so that, once the drill bit 42 has been moved to a final drilling position within the bone 1, the measuring instrument 44 may be coupled to the drill sleeve without uncoupling the drilling tool 43 therefrom. In particular, since the measuring instrument 44 is flexible, it can bend away from the longitudinal axis of the drill sleeve to permit coupling of the measurement instrument 44 thereto without requiring the removal of the drilling tool 43. Thus, the measuring instrument 44 may be used to measure a length of the screw to be inserted into the drilled hole without disengagement of the drilling tool 43. The measuring instrument 44 includes a scale therealong for indicating a length of the screw to be inserted into the drilled hole.

Although the exemplary embodiments were described with reference to a proximal femur, it will be appreciated that the principle of the invention can also be applied to bone plates for other bones. For example, the invention can also be provided for the distal femur, the tibia or other long bones. It will be appreciated that the shape and dimensioning of the bone plate and of the wire insertion device, the positioning device and the aiming device, if any, can be adapted in accordance with the case of application without impairing the principle of the invention.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A method for attaching a bone plate to a bone, comprising the steps of:
    placing a first surface of a wire insertion device against the bone;
    inserting a reference wire through an opening of the wire insertion device extending through the wire insertion device from the first surface of the wire insertion device to a second surface of the wire insertion device opposing the first surface;
    removing the wire insertion device from the reference wire inserted into the bone; and
    positioning a bone plate on the bone by moving the bone plate in a transverse direction relative to a longitudinal axis of the reference wire so that the reference wire is received within a slot of the bone plate, the bone plate including a first surface facing toward the bone and a second surface opposing the first surface, the slot extending through the bone plate from the first surface to the second surface and open to a lateral side surface connecting edges of the first and second surfaces.

2. The method according to claim 1, comprising the step of mounting a positioning device on the bone plate before the step of positioning the bone plate on the bone.

3. The method according to claim 2, wherein the second surface of the bone plate includes a plurality of alignment openings extending therein, each of the plurality of alignment openings sized and shaped to receive a corresponding alignment protrusion extending from a surface of the positioning device so that the positioning device is maintained in a desired position relative to the second surface of the bone plate before coupling the positioning device to the bone plate.

4. The method according to claim 2, wherein the positioning device includes a through hole extending therethrough and open to a lateral side surface of the positioning device via a slot, so that the slot of the positioning device is aligned with the slot of the bone plate when the positioning device is coupled to the bone plate in the desired position and the reference wire may be slid into the slot of the positioning device when the bone plate is slid on to the reference wire.

5. The method according to claim 4, comprising the step of advancing a protection sleeve along the reference wire until a distal end of the protection sleeve is received within the slot and the through hole of the positioning device, the protection sleeve including a first axial passageway and a second axial passageway parallel thereto, the first axial passageway sized and shaped to receive the reference wire.

6. The method according to claim 5, comprising the step of inserting through the second axial passageway of the protection sleeve one of a drill sleeve and a tool for producing a hole in the bone.

7. The method according to claim 5, comprising the step of inserting a bone anchor into the bone through the second axial passageway of the protection sleeve, through the through hole of the positioning device to engage a through hole of the bone plate.

8. The method according to claim 5, wherein a flexible measuring device is coupled to a drill sleeve inserted through the second axial passageway of the protection sleeve, the measuring device bending away from a longitudinal axis of the drill sleeve upon insertion of a hole producing tool into drill sleeve.

9. The method according to claim 2, comprising the step of mounting an aiming device on the positioning device, the aiming device being configured to maintain a drill sleeve along a desired path on which a hole is to be drilled into the bone.

10. The method according to claim 1, comprising the step of inserting an orientation wire into the bone before placing the wire insertion device against the bone, the wire insertion device being placed against the bone such that the reference wire lies in a plane parallel to a plane in which the orientation wire lies.

* * * * *